United States Patent
Miyajima et al.

(10) Patent No.: US 11,389,550 B2
(45) Date of Patent: Jul. 19, 2022

(54) NANOPARTICLE, CONTRAST AGENT FOR MAGNETIC RESONANCE IMAGING CONTAINING SAME, AND LIGAND COMPOUND

(71) Applicants: RIKEN, Saitama (JP); NATIONAL INSTITUTES FOR QUANTUM SCIENCE AND TECHNOLOGY, Chiba (JP)

(72) Inventors: Daigo Miyajima, Saitama (JP); Toshiaki Takeuchi, Saitama (JP); Seunghyun Sim, Saitama (JP); Takuzo Aida, Saitama (JP); Ichio Aoki, Chiba (JP)

(73) Assignees: RIKEN, Wako (JP); NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 14 days.

(21) Appl. No.: 16/624,946

(22) PCT Filed: Jun. 27, 2018

(86) PCT No.: PCT/JP2018/024416
§ 371 (c)(1),
(2) Date: Dec. 20, 2019

(87) PCT Pub. No.: WO2019/004297
PCT Pub. Date: Jan. 3, 2019

(65) Prior Publication Data
US 2020/0330617 A1    Oct. 22, 2020

(30) Foreign Application Priority Data

Jun. 28, 2017   (JP) .............................. JP2017-126755

(51) Int. Cl.
| | |
|---|---|
| *A61B 5/055* | (2006.01) |
| *A61K 49/10* | (2006.01) |
| *A61K 49/18* | (2006.01) |
| *C07C 309/14* | (2006.01) |
| *A61K 49/06* | (2006.01) |
| *B82Y 5/00* | (2011.01) |
| *B82Y 30/00* | (2011.01) |

(52) U.S. Cl.
CPC .......... *A61K 49/10* (2013.01); *A61K 49/1824* (2013.01); *C07C 309/14* (2013.01); *A61K 49/06* (2013.01); *A61K 49/1833* (2013.01); *A61K 2123/00* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | |
|---|---|---|
| 3,123,542 A | 3/1964 | Mandel et al. |
| 2010/0166664 A1 | 7/2010 | Butts et al. |
| 2010/0166665 A1 | 7/2010 | Butts et al. |
| 2010/0166666 A1 | 7/2010 | Butts et al. |
| 2011/0104072 A1 | 5/2011 | Bales et al. |
| 2013/0184444 A1 | 7/2013 | Bawendi et al. |
| 2014/0056819 A1 | 2/2014 | Butts et al. |
| 2014/0056821 A1 | 2/2014 | Bonitatibus, Jr. et al. |
| 2014/0147387 A1 | 5/2014 | Butts et al. |
| 2016/0038617 A1 | 2/2016 | Bales et al. |
| 2016/0296641 A1 | 10/2016 | Butts et al. |

FOREIGN PATENT DOCUMENTS

| | | |
|---|---|---|
| CN | 102639153 A | 8/2012 |
| CN | 104740654 A | 7/2015 |
| CN | 106068128 A | 11/2016 |
| CN | 106390146 A | 2/2017 |
| JP | 2016/221482 A | 12/2016 |
| RU | 2012116880 A | 12/2013 |
| RU | 2526181 C2 | 8/2014 |
| WO | WO-2013/090601 A2 | 6/2013 |
| WO | WO-2016/044068 A2 | 3/2016 |

OTHER PUBLICATIONS

Office Action issued in Russian Patent Application No. 2019143780, dated Aug. 27, 2021 and corresponding English Translation.
Corot et al., Recent advances in iron oxide nanocrystal technology for medical imaging, *Advanced Drug Delivery Reviews*, 58:1471-1504 (2006).
International Preliminary Report on Patentability for PCT/JP2018/024416, dated Jan. 9, 2020.
International Search Report for PCT/JP2018/024416, dated Sep. 4, 2018.

(Continued)

*Primary Examiner* — Michael G. Hartley
*Assistant Examiner* — Melissa J Perreira
(74) *Attorney, Agent, or Firm* — Marshall, Gerstein & Borun LLP

(57) ABSTRACT

Provided is a novel nanoparticle, a contrast agent for magnetic resonance imaging containing the same, and a ligand compound used for production of the nanoparticle. The present invention relates to a nanoparticle including: a metal particle containing iron oxide; and a ligand which is bound to a metal atom on a surface of the metal particle and is represented by formula (3):

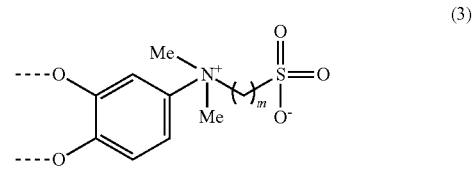

(3)

where m is an integer of 1 to 4, and a broken line represents a coordinate bond with a metal atom on the surface of the metal particle.

9 Claims, 6 Drawing Sheets

(56) References Cited

OTHER PUBLICATIONS

Kim et al., Large-Scale Synthesis of Uniform and Extremely Small-Sized Iron Oxide Nanoparticles for High-Resolution $T_1$ Magnetic Resonance Imaging Contrast Agents, *J Am. Chem. Sci.*, 133:12624-12631 (2011).
Wei et al., Compact Zwitterion-Coated Iron Oxide Nanoparticles for Biological Applications, *Nano Letters*, 12(1):22-25 (2012).
Wei et al., Compact zwitterion-coated iron oxide nanoparticles for *in vitro* and *in vivo* imaging, *Integr. Biol.*, 5:108-114 (2013).
Wei et al., Exceedingly small iron oxide nanoparticles as positive MRI contrast agents, *Proc. Natr. Acad. Sci.*, 114(9):2325-2530 (2017).
Office Action, Singapore Patent Application 11201912664W, dated Apr. 22, 2021.
Office Action For Chinese Application No. 201880041378.2 dated May 18, 2022.

[FIG. 1]
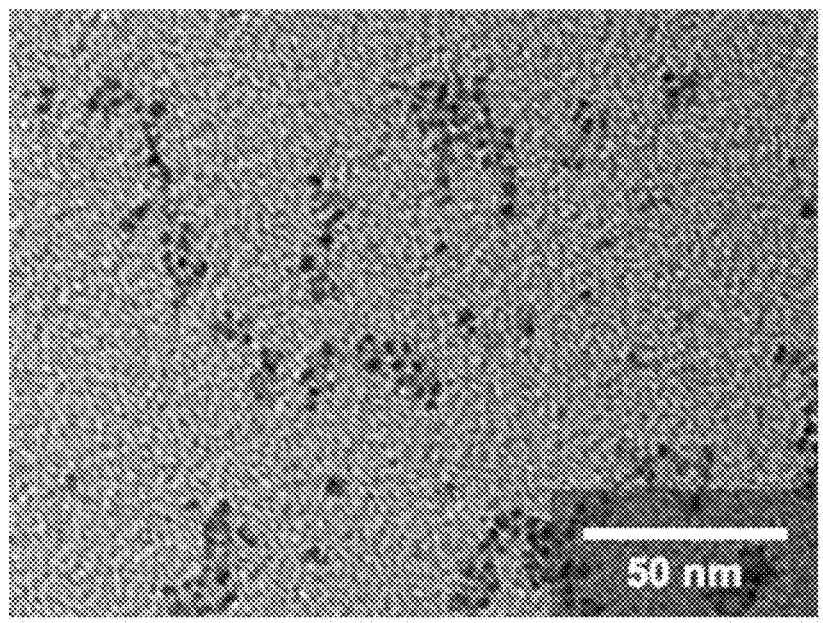

[FIG. 2]
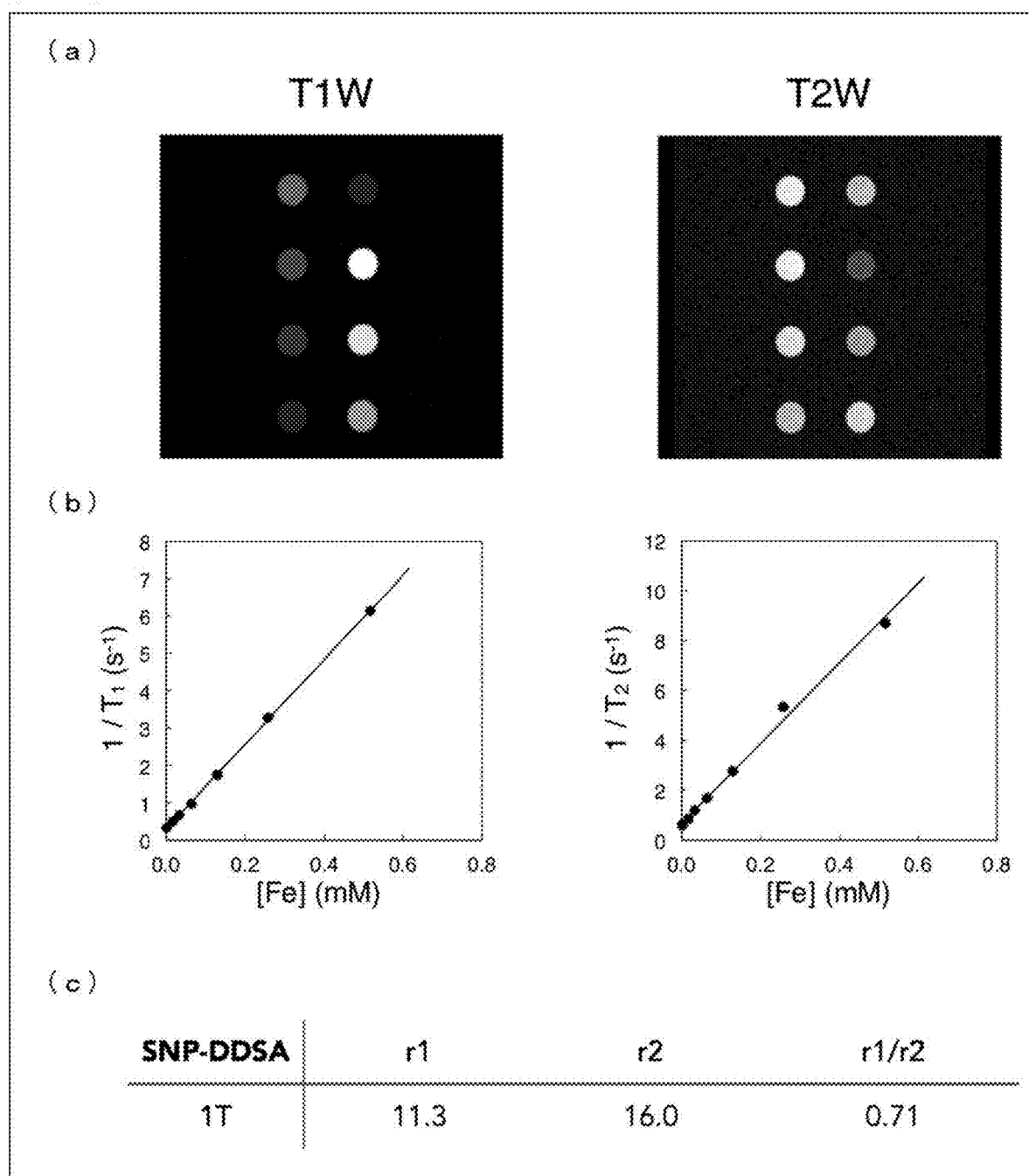

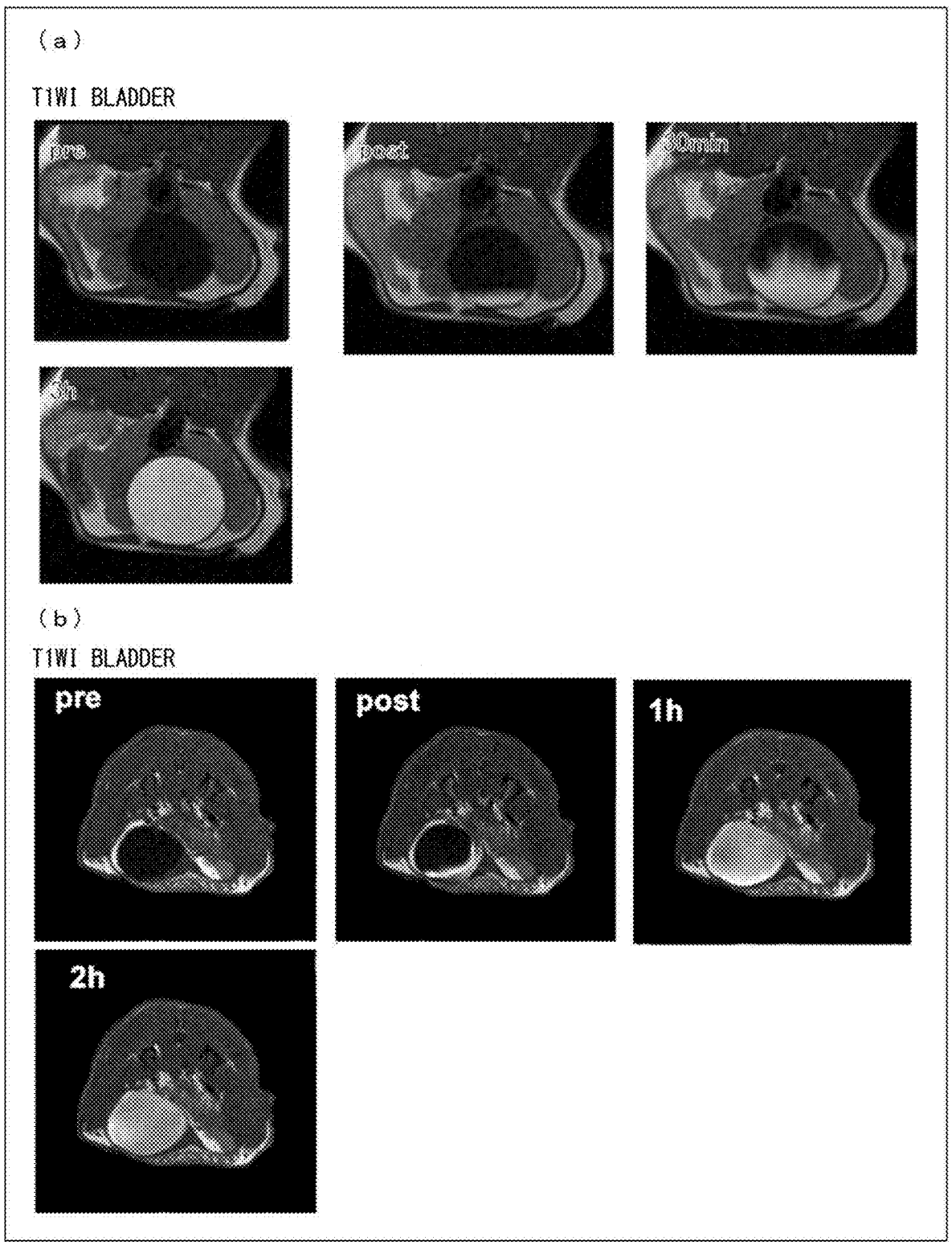

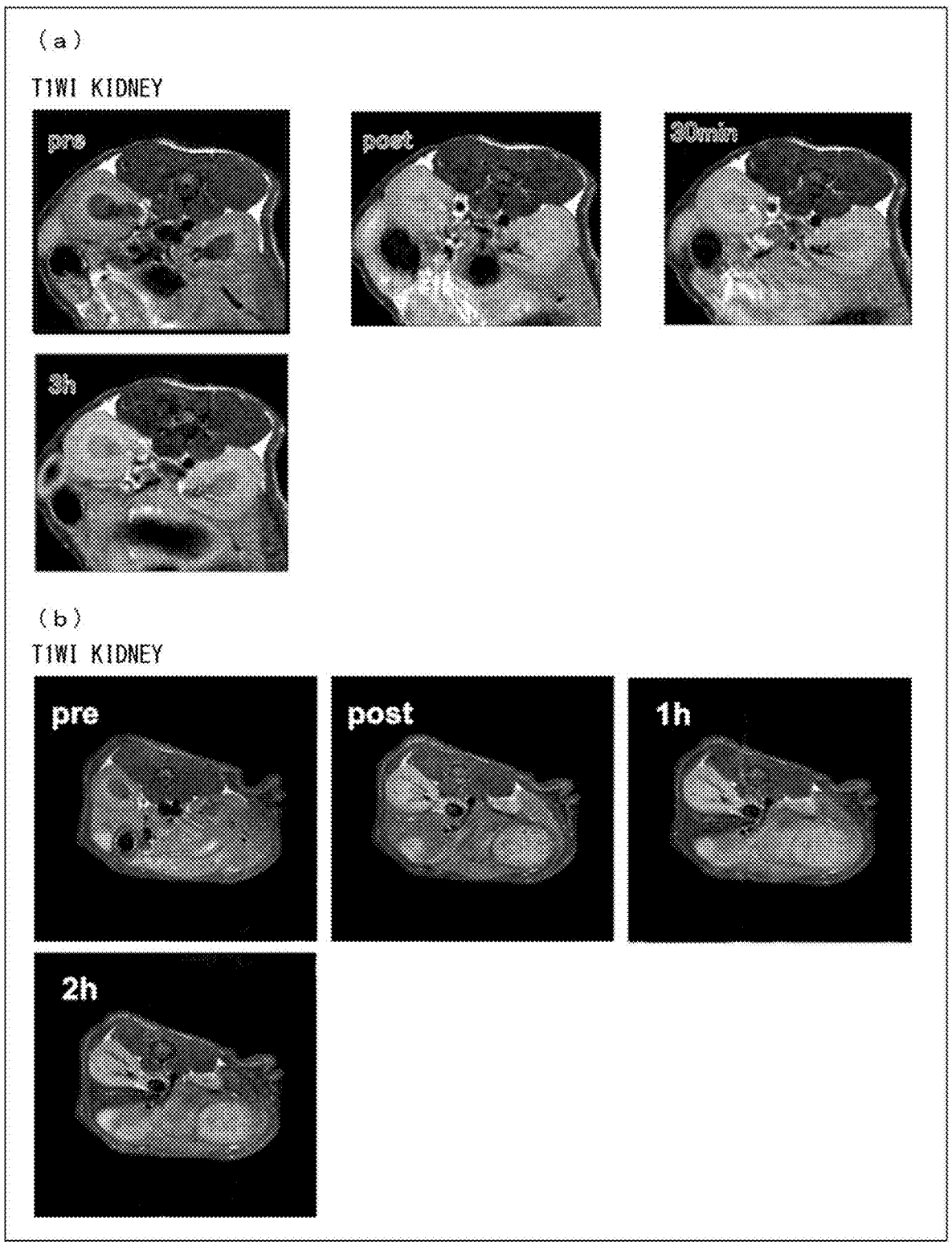

[FIG. 5]

[FIG. 6]
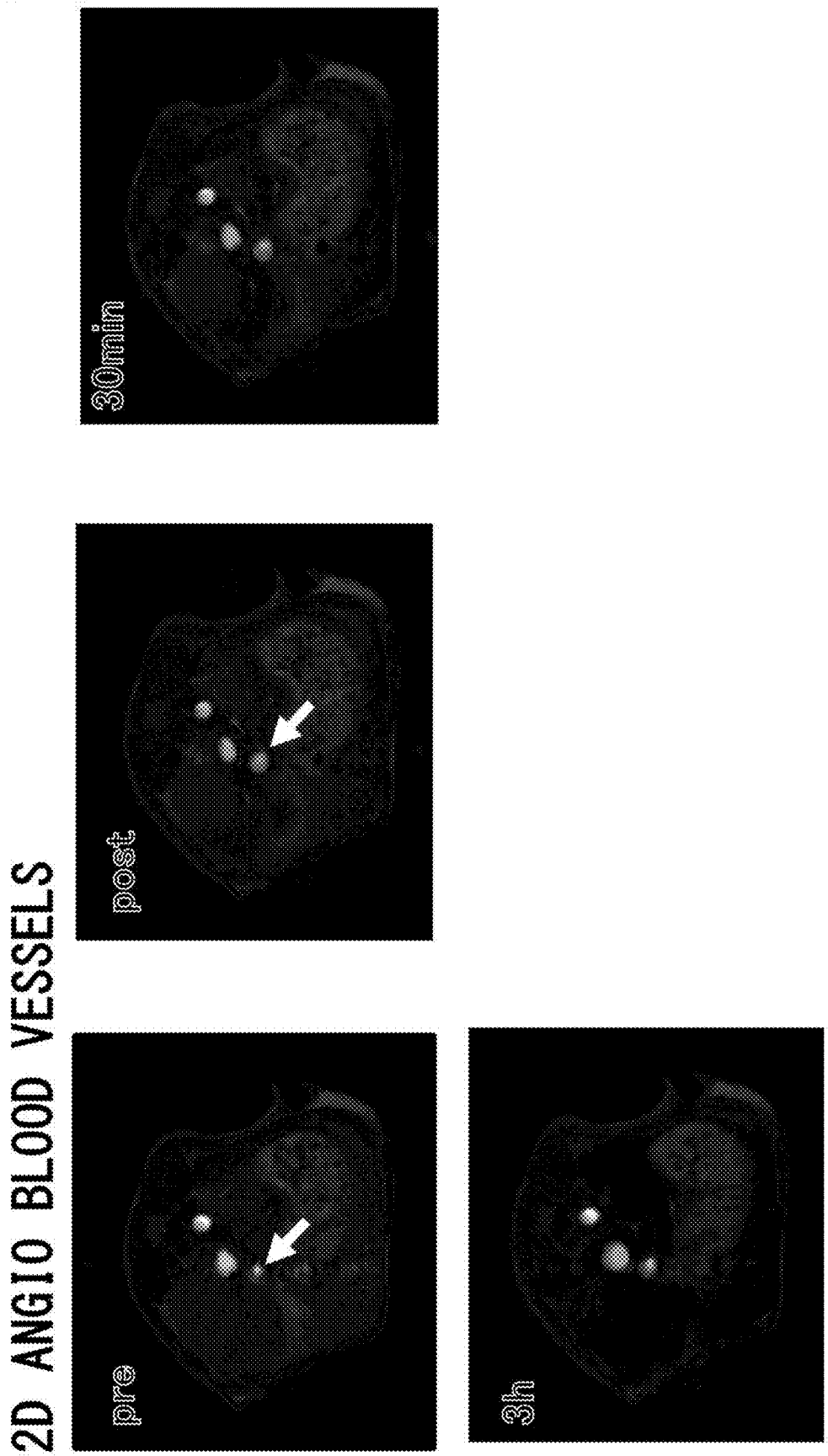

NANOPARTICLE, CONTRAST AGENT FOR MAGNETIC RESONANCE IMAGING CONTAINING SAME, AND LIGAND COMPOUND

CROSS REFERENCE TO RELATED APPLICATIONS

This application is a U.S. National Stage of International Application No. PCT/JP2018/024416, filed Jun. 27, 2018, which claims the benefit of Japanese Patent Application No. 2017-126755, filed Jun. 28, 2017, each of which is fully incorporated herein by reference.

TECHNICAL FIELD

The present invention relates to a novel nanoparticle, a contrast agent for magnetic resonance imaging containing the same, and a ligand compound used for production of the nanoparticle.

BACKGROUND ART

Magnetic resonance imaging (MRI), which has been playing an important role in clinical diagnostic imaging, is becoming an important tool also in the field of biomedical research in recent years.

Diagnostic imaging and a contrast agent used for the diagnostic imaging are a technology used for examination of an organ, tissue, and the like of a living organism. MRI, in particular, is a technology which, on the basis of magnetic properties of atoms, creates an elaborate cross-sectional image and an elaborate three-dimensional image of a tissue and an organ of a living organism with use of an intense magnetic field and a high-frequency radio signal.

MRI is an effective technique for obtaining a two- or three-dimensional image of all water-containing tissues and organs.

When converged electromagnetic wave pulses enter hydrogen atoms that are aligned by magnetism in a target tissue, the hydrogen atoms return signals as a result of relaxation of protons. On the basis of a slight difference between signals from various tissues, MRI can identify an organ and indicate a potential contrast between a benign tissue and a malignant tissue. MRI is useful for detection of a tumor, bleeding, an edema, and the like.

Note that a "contrast agent for MRI" refers to a drug which enables detection of a lesion area or examination of a blood flow in a blood vessel, a function of each organ, and the like, by (i) changing relaxation times ($T_1$, $T_2$) of water in a living organism mainly by shortening the relaxation times ($T_1$, $T_2$) and (ii) thus enhancing a contrast between different tissues.

The contrast agent for MRI is expected to have the following properties: that the contrast agent exhibits a contrast effect quickly after administration; that the contrast agent has no adverse effect on a living organism; and that 100% of the contrast agent is eliminated from the living organism. The contrast agent for MRI can be distributed in blood and extracellular fluid by, for example, intravenous administration. Then, the contrast agent is excreted to urine via the river preferably within 2 hours, more preferably within 1 hour. The contrast agent distributed in the extracellular fluid is in itself not directly imaged by MRI. The contrast agent promotes relaxation of protons in tissues in the area in which the contrast agent has been distributed. This is mainly called a $T_1$-shortening effect, and allows the contrast agent to exhibit a contrast effect in a $T_1$-weighted image (signals are enhanced). The contrast agent causes a change in relaxation time of a tissue occupied by the contrast agent.

On the other hand, in a case where a concentration of the contrast agent is increased to a certain level or higher, the signal is attenuated by $T_2$- and $T_2^*$-shortening effects. As such, an optimum concentration for allowing signal intensity to be increased varies depending on the purpose of performing contrast imaging.

Degrees of $T_1$- and $T_2$-relaxation shortening effects in a magnetic body, i.e., efficiencies in shortening relaxation times of protons are represented as relaxation rate (R). A relaxation rate $R_1$ and a relaxation rate $R_2$ are represented as a reciprocal of a longitudinal relaxation time $T_1$ and a reciprocal of a transverse relaxation time $T_2$, respectively, of MRI ($R_1=1/T_1$, $R_2=1/T_2$). A relaxation rate per unit concentration is represented as relaxivity (r). Longitudinal relaxivity is represented as $r_1$, and transverse relaxivity is represented as $r_2$. An $R_1/R_2$ ratio and an $r_1/r_2$ ratio are each used as a parameter for evaluating a relaxivity of a contrast agent for MRI.

In particular, a contrast agent which utilizes $T_1$ relaxation and is used for the purpose of enhancing signals on a $T_1$-weighted image is referred to as a $T_1$ shortening contrast agent or a positive contrast agent. The positive contrast agent causes a signal increase in tissues occupied by the positive contrast agent. A contrast agent which utilizes $T_2$ relaxation and is used for the purpose of attenuating signals on a $T_2$-weighted image is referred to as a $T_2$ shortening contrast agent or a negative contrast agent. The negative contrast agent causes a signal decrease in tissues occupied by the negative contrast agent. $T_1$-weighted MRI has been attracting attention in recent years because, as compared to $T_2$-weighted MRI, $T_1$-weighted MRI has a small artifact and exhibits a high spatial resolution. In order to obtain a $T_1$-weighted MR image exhibiting high contrast, it is essential to use the positive contrast agent which enhances MRI contrast by changing relaxation times of water protons.

In particular, an $r_1/r_2$ ratio of a contrast agent is an important value for evaluation of the contrast agent. A high $r_1/r_2$ ratio of a positive contrast agent enables providing a good $T_1$-weighted MR image.

A gadolinium (Gd)-based chelate and a gadolinium oxide nanoparticle can be clinically used as a positive contrast agent, and exhibits excellent $T_1$ contrast due to having high $r_1$ and low $r_2$ (i.e., a high $r_1/r_2$ ratio). However, Gd-based compounds are known to have toxicity to an elderly person and a patient with renal failure.

Iron oxide-based compounds, on the other hand, have an extremely low toxicity as compared with the Gd-based compounds. As such, research and development is being conducted on iron oxide-based nanoparticles as an alternative material to Gd, which is the current mainstream in the market (Non-Patent Literature 1).

So far, research and development has been conducted on nanoparticles to be applied to medical uses (e.g., for diagnosis, treatment, or the like). As an aspect of a nanoparticle to be applied to a living organism, there is known a nanoparticle including (i) a core particle consisting of a metal material and (ii) a molecule of various kinds, such as a polymer, with which a surface of the core particle is coated. For example, there have been reported (i) a method for producing iron oxide particles (ESIONs) having a size of 4 nm or less and (ii) a positive contrast agent for MRI which positive contrast agent contains nanoparticles including (a) ESIONs and (b) polyethylene glycol phosphate (PO-PEG)

with which the ESIONs are coated (Non-patent Literature 2). There has also been reported a nanoparticle having a structure in which zwitterionic dopamine sulfonate (ZDS) is bound to a surface of an iron oxide nanoparticle serving as a core particle (Non-Patent Literature 3 and Patent Literature 1). Properties of such nanoparticles (ZDS-SPIONs) when used as a positive contrast agent have also been reported (Patent Literature 2 and Non-patent Literature 4).

CITATION LIST

Patent Literatures

[Patent Literature 1]
International Publication No. WO2013/090601 (Publication Date: Jun. 20, 2013)
[Patent Literature 2]
International Publication No. WO2016/044068 (Publication Date: Mar. 24, 2016)

Non-Patent Literatures

[Non-Patent Literature 1]
Corot et al., Advanced Drug Delivery Reviews, 58, 1471-1504, 2006
[Non-Patent Literature 2]
Byung Hyo Kim et al., J Am. Chem. Sci., 133, 12624-12631, 2011
[Non-Patent Literature 3]
He Wei et al., Integr. Biol., 5, 108-114, 2013
[Non-Patent Literature 4]
He Wei et al., Proc. Natr. Acad. Sci., 114(9), 2325-2330, 2017

SUMMARY OF INVENTION

Technical Problem

There is still a demand for (i) a novel nanoparticle that sufficiently meets the following conditions: exhibiting a behavioral stability in a living organism while having an excellent contrast ability; having a low toxicity to a living organism; and having a good storage stability and (ii) a ligand compound for coating the nanoparticle. Further, there is a need for development of a contrast agent for magnetic resonance imaging containing the nanoparticle.

Solution to Problem

In order to solve the above problem, the present invention includes in its scope any one aspect below.

<1> A nanoparticle, including: a metal particle containing iron oxide; and a ligand which is bound to a metal atom on a surface of the metal particle and is represented by formula (3):

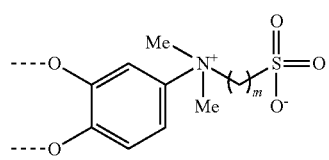

(3)

where m is an integer of 1 to 4, and a broken line represents a coordinate bond with a metal atom on the surface of the metal particle.

<2> (3,4-dihydroxyphenyl)(dimethyl)(3-sulfonate propyl)ammonium.

Note that a structural formula of (3,4-dihydroxyphenyl)(dimethyl)(3-sulfonate propyl)ammonium is represented by formula (2). In the specification of the present application, the above compound may be abbreviated as "DDSA", and a ligand represented by formula (1) (described later) which ligand is the above compound in a state in which the above compound is bound to a metal atom on a surface of a metal particle may also be abbreviated as "DDSA".

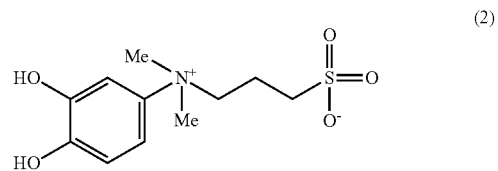 [SMILES: C[N+](C)(CCCS(=O)(=O)[O-])c1ccc(O)c(O)c1]

(2)

Advantageous Effects of Invention

The present invention is expected to enable providing (i) a novel nanoparticle, (ii) a contrast agent for magnetic resonance imaging containing the same, in particular, a positive contrast agent having a good relaxivity, and (iii) a novel ligand compound used for production of the nanoparticle.

BRIEF DESCRIPTION OF DRAWINGS

FIG. 1 is an image of a nanoparticle (iron oxide particle (SNP)-ligand (DDSA)) of the present invention observed by a transmission electron microscope (TEM).

FIG. 2 is views illustrating results of estimation of relaxivity of SNP-DDSA in PBS in a case where a 1 tesla (T) MRI is used, the SNP-DDSA including an iron oxide particle of 1.8 nm in diameter as a core. (a) of FIG. 2 illustrates a result of measurement of relaxation times in PBS of SNP-DDSA obtained by diluting SNP-DDSA in sequence. (b) of FIG. 2 is views each obtained by plotting a relaxation time with respect to an iron atom concentration in SNP-DDSA. (c) of FIG. 2 shows values of relaxivities r 1 and $r_2$ determined from an inclination of the plotted line in (b) of FIG. 2, and a $r_1/r_2$ value.

(a) of FIG. 3 shows images of a bladder of a mouse to which a contrast agent containing SNP-DDSA of Example 2 was administered, which images were obtained as a result of MRI measurement carried out over time, respectively at the following timings: prior to the administration (pre), immediately after the administration (post), 30 minutes after the administration (30 min), and 3 hours after the administration (3 h). (b) of FIG. 3 shows images of the bladder of the mouse to which the contrast agent containing SNP-DDSA of Example 2 was administered, which images were obtained as a result of MRI measurement carried out over time, respectively at the following timings: prior to the administration (pre), immediately after the administration (post), 1 hour after the administration (1 h), and 2 hours after the administration (2 h).

(a) of FIG. 4 shows images of a kidney of a mouse to which a contrast agent containing SNP-DDSA of Example 2 was administered, which images were obtained as a result of MRI measurement carried out over time, respectively at the following timings: prior to the administration (pre), immediately after the administration (post), 30 minutes after the administration (30 min), and 3 hours after the administration (3 h). (b) of FIG. 4 shows images of the kidney of the mouse to which the contrast agent containing SNP-DDSA of Example 2 was administered, which images were obtained as a result of MRI measurement carried out over time, respectively at the following timings: prior to the administration (pre), immediately after the administration (post), 1 hour after the administration (1 h), and 2 hours after the administration (2 h).

FIG. 5 shows images of a liver of a mouse to which a contrast agent containing SNP-DDSA of Example 2 was administered, which images were obtained as a result of MRI measurement carried out over time.

FIG. 6 shows images of blood vessels of a mouse to which a contrast agent containing SNP-DDSA of Example 2 was administered, which images were obtained as a result of MR angiography carried out over time.

DESCRIPTION OF EMBODIMENTS

The description below deals with an embodiment of the present invention in detail.

[Definitions of Terms]

Generally, the term "nanoparticle" refers to a particle having a particle diameter in an order of nanometers, and ordinarily refers to a particle having a particle diameter of less than 1 μm. Details of particle diameter will be discussed later in a section of particle diameter.

The term "ligand" or "ligand compound" refers to a compound which (i) has a group capable of forming a coordinate bond with a metal atom on a surface of a metal particle and (ii) is used as a modifier on the surface of the metal particle for allowing the metal particle to be stably dispersed in water. As used herein, the term "ligand" or "ligand compound" refers to (i) a case in which the compound has not been bound by a coordinate bond to a surface of a metal particle and/or (ii) a case in which the compound has a molecular structure in which the compound has been bound by a coordinate bond to a surface of a metal particle.

As used herein, the term "subject" refers to a given organism to which a contrast agent for MRI, a nanoparticle, or a composition containing the nanoparticle of the present invention can be administered for the purpose of, for example, experiment, diagnosis, and/or treatment. As an example, the subject is a human.

The following description will discuss a nanoparticle, a contrast agent for MRI, and a compound in accordance with the present invention.

[1. Nanoparticle]

The nanoparticle in accordance with the present invention is a nanoparticle including: a metal particle containing iron oxide; and a ligand which is bound to a metal atom on a surface of the metal particle and is represented by the following formula (3), wherein the ligand is preferably a ligand represented by the following formula (1).

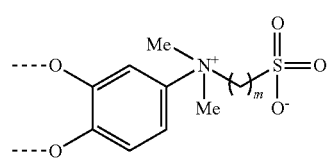

(3)

In the above formula (3), m is an integer of 1 to 4, and a broken line represents a coordinate bond with a metal atom on the surface of the metal particle.

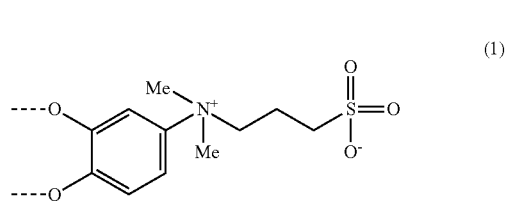

(1)

In the above formula (1), a broken line represents a coordinate bond with the metal atom on the surface of the metal particle.

Further, a nanoparticle in accordance with another aspect of the present invention is a nanoparticle including: a metal particle containing iron oxide; and a ligand which is bound to a metal atom on a surface of the metal particle and is represented by the above formula (3), where m is an integer of 1, 2, or 4.

In an embodiment of the present invention, the nanoparticle of the present invention is a nanoparticle including: a metal particle containing iron oxide; and a ligand which is bound to a metal atom on a surface of the metal particle and is represented by the above formula (3), where m is 2 or 4, more preferably 4.

That is, the nanoparticle in accordance with the present invention is a particle which includes a metal particle in a center part (core) of the particle and in which a ligand compound is bound to an outer surface of the metal particle so as to coat the metal particle.

The nanoparticle of the present invention enables prevention of agglomeration of nanoparticles, and exhibits stable particle properties even in, for example, a solution containing the nanoparticle at a high concentration. Such a nanoparticle can be expected to both (i) ensure low saturation magnetization and thus enable obtaining a clear $T_1$-weighted image and (ii) facilitate renal excretion and thus enable good renal clearance.

(Metal Particle)

The metal particle contains iron oxide. In an embodiment of the present invention, the metal particle is an iron oxide particle containing only iron oxide.

In an embodiment of the present invention, the metal particle may contain iron oxide and at least one metal derivative other than iron oxide. Further, the metal particle may contain at least one metal element other than iron (Fe). As the other metal element, the metal particle may further contain, as necessary, at least one selected from the group consisting of gadolinium (Gd), manganese (Mn), cobalt (Co), nickel (Ni), and zinc (Zn).

In still another embodiment of the present invention, the metal particle may consist of iron oxide alone or may contain ferrite derived from iron oxide. Ferrite is an oxide represented by formula: $(Fe^{2+}, M)_3O_4$ where M is preferably a transition metal ion selected from $Zn^{2+}$, $Co^{2+}$, $Mn^{2+}$, and $Ni^{2+}$.

A material known as super paramagnetic iron oxide (SPIO) may be also suitably used. Such a material is represented by general formula: $[Fe_2O_3]_x[Fe_2O_3(M^{2+}O)]_{1-x}$ (where x=0 or 1). $M^{2+}$ may be a divalent metal ion of, for example, Fe, Mn, Ni, Co, Zn, magnesium (Mg), copper (Cu), or a combination thereof. Note that the material is magnetite ($Fe_3O_4$) in a case where the metal ion ($M^{2+}$) is a ferrous iron ($Fe^{2+}$) and x=0, and the material is maghemite ($\gamma$-$Fe_2O_3$) in a case where x=1.

In an embodiment of the present invention, iron oxide is magnetic oxide of iron, and may be magnetite ($Fe_3O_4$), maghemite (γ-Fe₂O₃), or a mixture thereof. A particle of the magnetic iron oxide is a super paramagnetic nanoparticle.

In still another embodiment of the present invention, in a case where the iron oxide particle contains derivative(s) of one or more metallic elements other than iron, the derivative(s) of the respective metal element(s) may differ in kind. That is, the iron oxide particle may contain an oxide, a nitride, and the like. In another embodiment of the present invention, a core particle may contain a derivative (e.g., FePt and FeB) of iron other than iron oxide which derivative has an iron element other than iron oxide.

A metal particle in accordance with an embodiment of the present invention may be a metal particle produced by a well-known method such as a method disclosed in Patent Literature 1, Non-patent Literature 2, Non-patent Literature 3, or the like, or may be a commercially available metal particle. For example, the metal particle may be an iron oxide particle produced by a coprecipitation method or a reduction method.

(Particle Diameter of Metal Particle)

As used herein, the term "particle diameter" refers to an "average particle diameter" unless otherwise noted.

As used herein, the term "particle diameter" means a diameter of a maximum inscribed circle of a two-dimensional shape of a particle observed with use of a transmission electron microscope (TEM). For example, in a case where the two-dimensional shape of the particle is substantially a circle, the "particle diameter" means a diameter of the circle.

In a case where the two-dimensional shape of the particle is substantially an ellipse, the "particle diameter" means a minor axis of the ellipse. In a case where the two-dimensional shape of the particle is substantially a square, the "particle diameter" means a length of a side of the square. In a case where the two-dimensional shape of the particle is substantially a rectangle, the "particle diameter" means a length of a short side of the rectangle.

Examples of a method for confirming a value of an average particle diameter is in a predetermined range include a method of observing 100 particles with use of a transmission electron microscope (TEM) to measure the particle diameter of each particle and find an average value of the particle diameters of the 100 particles.

An iron oxide particle in accordance with an embodiment of the present invention preferably has a diameter of 5 nm or less, more preferably has a diameter of 4 nm or less, more preferably has a diameter of 3 nm or less, even more preferably has a diameter of 2 nm or less, and most preferably has a particle diameter of 1 nm or less. Having a particle diameter of 2 nm or less makes the iron oxide particle more useful as a positive contrast agent for high-field MRI of 3 tesla (T) or more. Further, an iron oxide particle having a particle diameter of 2 nm or less, preferably 1 nm or less, enables achieving a higher signal-to-noise ratio when used for high-magnetic field MRI of 7 T or more. This may enable measurement with a higher spatial resolution and in a shorter period of time.

An iron oxide particle of the present invention has an average particle diameter of preferably 5 nm or less, more preferably 4 nm or less, more preferably 3 nm or less, even more preferably 2 nm or less. As an example, the average particle diameter is 1.8 nm. It is preferable that the average particle diameter of the iron oxide particle be as small as possible. As an example, the average particle diameter is 0.5 nm or more, or 0.6 nm or more.

In an embodiment of the present invention, it is preferable that properties of the nanoparticle contained in the contrast agent for MRI are as uniform as possible among the individual nanoparticles. Accordingly, it is preferable that the metal particle serving as the core of the nanoparticle be uniform in size and shape. As an example, a uniformity of the metal particle in particle diameter is within a range of ±1 nm of the average particle diameter of the metal particle. As another example, the uniformity of the metal particle in particle diameter is within a range of ±0.5 nm of the average particle diameter of the metal particle. In another embodiment of the present invention, it is preferable that as many small particles as possible be contained each as the metal particle which serves as the core of the nanoparticle contained in the contrast agent for MRI. As an example, a ratio of the number of metal particles having a particle size of 5 nm or more to the number of all the metal particles is 30% or less, preferably 10% or less, more preferably 5% or less. As another example, a ratio of the number of metal particles having a particle size of 4 nm or more to the number of all the metal particles is 30% or less, preferably 10% or less, more preferably 5% or less. As yet another example, a ratio of the number of metal particles having a particle size of 3 nm or more to the number of all the metal particles is 30% or less, preferably 10% or less, more preferably 5% or less.

(Particle Diameter of Nanoparticle)

The particle diameter of the nanoparticle increases as a thickness of the ligand with which the metal particle is coated increases. Measurement of the particle diameter of the nanoparticle, however, is difficult. Ordinarily, a hydrodynamic diameter (HD) of the nanoparticle as measured in a solution of the nanoparticle is treated as an index for the size of the nanoparticle. As an example, the nanoparticle has an average HD of 30 nm or less, preferably 10 nm or less. As another example, the nanoparticle has an average HD of 7 nm or less, preferably 6 nm or less, preferably 5 nm or less, preferably 4 nm or less, more preferably 3 nm or less.

Note that it has been confirmed that the contrast ability of the contrast agent for MRI is affected by the particle diameter of the metal particle serving as the core.

(Ligand)

The ligand compound in accordance with the present invention is a compound represented by the following formula (4):

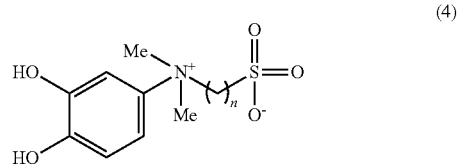

(4)

where n is an integer of 1 to 4.

In an aspect of the present invention, the ligand compound in accordance with the present invention is (3,4-dihydroxyphenyl) (dimethyl)(3-sulfonate propyl)ammonium (DDSA) represented by formula (2) below. In a ligand substitution reaction (described later), hydrogen ions are desorbed from two hydroxyl groups of the compound, and each remaining oxygen atom forms a coordinate bond with a metal atom on the surface of the metal particle. Thus produced is the nanoparticle of the present invention. The ligand bound by a coordinate bond to the metal atom on the surface of the metal particle has a structure represented by the above formula (1).

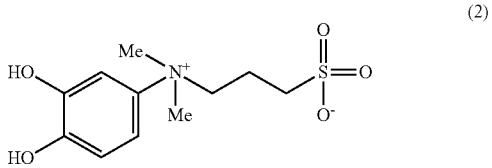 [SMILES: C[N+](C)(CCCS(=O)(=O)[O-])c1ccc(O)c(O)c1]

(2)

Note that the metal atom with which the oxygen atom of the ligand of the present invention forms a coordinate bond is an atom located on the surface of the metal particle serving the core. For example, the metal atom is an iron atom.

The ligand of the present invention has a structure in which an ammonium group is directly bonded to a benzene ring. This allows the ligand of the present invention to have a molecular chain shorter than that of a conventionally known ligand, and accordingly allows a ligand layer to be thinner. Further, it is a characteristic of the ligand of the present invention that the ligand has a positive charge on a metal particle side and a negative charge on the outer surface of the core particle. As such, it can be expected that the nanoparticle of the present invention is less likely to undergo agglomeration of core particles in body fluid and thus is highly stable. Further, thinness of the ligand layer of the present invention reduces a distance from the metal atom. It can be accordingly expected that the nanoparticle of the present invention exhibits an excellent contrast ability resulting from an increase in the number of water molecules affected by the core particle, and the like.

The number (the number of ligands) of ligand molecules coordinated on the surface of the metal particle varies depending on a size, surface area, and the like of the metal particle. For example, in a case where the metal particle has a particle diameter of 1.8 nm, the number of ligands per metal particle is preferably 5 to 200, more preferably 10 to 50.

(Method for Producing Ligand)

A method for producing the ligand is not particularly limited. The ligand can be produced easily from a well-known raw material compound by a reaction well known to a person skilled in the art. For example, the ligand can be produced with reference to a method described in Wei H. et al., Nano Lett. 12, 22-25, 2012.

As an example, a synthesis method described in Examples can be suitably employed.

(Compound Bound to Metal Particle Other than Ligand)

The nanoparticle of the present invention may contain a component other than the ligand of the present invention. In an embodiment of the present invention, the nanoparticle may be (i) a nanoparticle in which a core particle itself has a fluorescent property or (ii) a nanoparticle which further contains a molecule such as a fluorescent molecule, a dye molecule, or the like bound to a surface of the core particle. In a case where the core particle itself has a fluorescent property or in a case where a fluorescent molecule or a dye molecule is introduced in the nanoparticle, the nanoparticle can be used not only as a contrast agent for MRI but also as a contrast agent for an optical image. In another embodiment of the present invention, the nanoparticle of the present invention may include a fluorescent molecule or a dye molecule which is bound by a covalent bond to the ligand of the present invention and is linked to the iron oxide particle via the ligand. After the nanoparticle is injected into a body, the fluorescent molecule is present on the surface of the iron oxide particle. The fluorescent molecule can thus be utilized for microscopic imaging and examination of localization of the nanoparticle. Examples of the fluorescent molecule and the dye molecule include rhodamine, fluorescein, nitrobenzoxadiazole (NBD), cyanine, green fluorescence protein (GFP), coumarin, and a derivative thereof.

In another embodiment of the present invention, the nanoparticle of the present invention may include at least one substance bound to the surface of the metal particle. Examples of such a substance include, but are not limited to, a peptide, a nucleic acid, a small molecule, or the like.

Further, another ligand other than the ligand of the present invention may be bound to the surface of the nanoparticle. For example, in a case where a ligand having a property of being accumulated specifically to a tumor is bound to the nanoparticle of the present invention, the nanoparticle can have a tumor-selective binding property.

Imparting such a tissue specificity to the contrast agent is preferable in order to (i) enhance a signal at a portion that is a subject of MRI measurement and (ii) thereby obtain information of a specific pathological condition or the like. A distribution of the contrast agent in a living organism depends on particle diameter, charge, surface chemistry, route of administration, and route of elimination.

Further, the nanoparticle of the present invention has an extremely low toxicity to a living organism. Accordingly, the nanoparticle is highly safe and faces few limitations in order to be put to various uses.

[2. Method for Producing Nanoparticle]

The following description will discuss a method for producing the nanoparticle. The method for producing the nanoparticle is not particularly limited, and can be a well-known method.

For example, the nanoparticle can be produced with reference to a method disclosed in Kim et al., J Am. Chem. Sci. 2011, 133, 12624-12631, Kim et al., J Am. Chem. Sci. 2013, 135, 2407-2410, and a method disclosed in Hyeon et al., J. Am. Chem. Soc., 133, 12624, 2011.

A method in accordance with an embodiment of the present invention for producing the nanoparticle includes the steps of (a) reacting a metal salt with an alkali metal salt of a carboxylic acid having 18 carbon atoms to form a metal-carboxylic acid complex, (b) heating the metal-carboxylic acid complex to synthesize a metal particle which serves as a core of the nanoparticle and whose surface is coated with a hydrophobic ligand, (c) converting the hydrophobic ligand on the surface of the metal particle serving as the core into a hydrophilic ligand having a carboxyl group to form a particle dispersible in a highly-polar solvent, and (d) reacting the metal particle coated with the hydrophilic ligand with the ligand compound of the present invention to substitute the hydrophilic ligand on the surface of the metal particle with the ligand of the present invention. The following describes each step in detail.

(Step (a))

The step (a) is a step in which a metal salt is reacted with an alkali metal salt of a carboxylic acid having 18 carbon atoms to form a metal-carboxylic acid complex.

Frist, a metal salt and an alkali metal salt of a carboxylic acid having 18 carbon atoms are dispersed in a solvent. Examples of the metal salt used for preparation of the metal-carboxylic acid complex include iron(III) chloride hexahydrate [$FeCl_3 \cdot 6H_2O$]. Examples of the alkali metal salt of the carboxylic acid having 18 carbon atoms include sodium oleate. Examples of the solvent include ethanol, water, hexane, and a mixture thereof. As an example, iron(III) chloride hexahydrate and sodium oleate are dispersed in a mixture of ethanol, water, and hexane. Subsequently, a resultant solution is stirred while being heated, preferably at 70° C., for 1 hour to 10 hours, preferably for 4 hours, and an organic layer is collected. The organic layer is washed with water once or more, more preferably 3 times to 4 times. The organic layer obtained is optionally dried.

(Step (b))

The step (b) is a step in which the complex obtained in the step (a) is reacted with a hydrophobic ligand to synthesize a nanoparticle in which a surface of a metal particle serving as a core is coated with the hydrophobic ligand.

For example, in an atmosphere of a gas selected from argon (Ar) and nitrogen, the following (i) and (ii) are added to the complex obtained in the step (a): (i) at least one detergent selected from the group consisting of a fatty acid having 18 carbon atoms, aliphatic alcohol having 18 carbon atoms, and aliphatic amine having 18 carbon atoms and (ii) a solvent selected from diphenyl ether and phenyloctyl ether. As an example, the detergent may be oleyl alcohol and the solvent may be diphenyl ether. Subsequently, a mixture thus obtained is heated from room temperature to a temperature of 180° C. to 300° C., and then is optionally stirred in this state for 10 minutes to several hours. As an example, the mixture is heated from 30° C. to 250° C. at a rate of 10° C./min, and is stirred at 250° C. for 30 minutes. As another example, the mixture is heated from 30° C. to 200° C. at a rate of 10° C./min, and is stirred at 200° C. for 30 minutes.

A resultant reaction solution is cooled down to room temperature. Then, acetone is added, a resultant mixture is centrifuged, and a supernatant is removed. This operation is repeated 2 times to 3 times, preferably 4 times to 5 times. A solution thus obtained is optionally dried. As an example, the operation of adding acetone, performing centrifugation, and removing the supernatant is repeated 3 times.

(Step (c))

The step (c) is a step in which the hydrophobic ligand, with which the surface of the nanoparticle obtained in the step (b) is coated, is substituted with a hydrophilic ligand having a carboxyl group to form a particle dispersible in a highly-polar solvent.

For example, in an atmosphere of a gas selected from Ar and nitrogen, the nanoparticle coated with the hydrophobic ligand is dispersed in a solvent, and then a hydrophilic ligand having a carboxyl group is added. Examples of the hydrophilic ligand having a carboxyl group include 2-[2-(2-methoxyethoxy)ethoxy]acetic acid (MEEA). Methanol is suitable as the solvent.

A reaction solution is reacted at room temperature or while being heated, preferably at 25° C. to 80° C. for approximately 1 hour to 15 hours, preferably 5 hours to 10 hours. As an example, the reaction is carried out by stirring the reaction solution at 50° C. for 7 hours. As an example, the reaction is carried out by stirring the reaction solution at 70° C. for 10 hours. As yet another example, the reaction is carried out by stirring the reaction solution at 70° C. for 5 hours.

The reaction solution is cooled down to room temperature. Then, a solvent selected from acetone and hexane is added, a resultant mixture is centrifuged, and a supernatant is removed. This operation can be repeated 2 times to 3 times, preferably 4 times to 5 times. A solution thus obtained may optionally be dried. As an example, the above operation is repeated 3 times.

(Step (d))

The step (d) is a step in which the metal particle obtained in the step (c) and coated with the hydrophilic ligand is reacted with the ligand compound of the present invention to obtain a nanoparticle in which a surface of the metal particle is coated with the ligand compound of the present invention.

Note that the metal particle coated with the hydrophilic ligand is reacted with the ligand compound of the present invention by being stirred for 1 hour to several tens of hours in an atmosphere of a gas selected from Ar and nitrogen and at room temperature or while being heated. As an example, the above reaction is carried out in an Ar atmosphere. A reaction temperature is 25° C. to 80° C. as an example, and 50° C. to 70° C. as another example. A stirring time is 5 hours to 7 hours as an example, and 24 hours as another example. As an example, stirring is performed at 70° C. for 12 hours. Subsequently, a resultant reaction solution is cooled down to room temperature, and a solvent is added. A resultant mixture is centrifuged, and a supernatant is removed. The solvent is not particularly limited, and may be selected from acetone, hexane, and the like. As an example, the solvent is acetone. The operation of adding the solvent, performing centrifugation, and removing the supernatant can be repeated a plurality of times. For example, the operation may be repeated 4 times to 5 times. As an example, this operation is repeated 3 times. Subsequently, a resultant solution containing the nanoparticle coated with the ligand compound of the present invention can be concentrated with use of a concentration column or the like of a centrifugal ultrafilter or the like. This concentration operation can be repeated a plurality of times, during which a solution such as PBS may be added at some point, and then the concentration operation may be repeated.

As an aspect of the present invention, the following description will discuss another method for producing a nanoparticle having an iron oxide particle as a core.

An iron oxide particle (SNP-OA) coated with oleic acid is suspended in a hexane solution. A resultant suspension is mixed with 1.7% tetramethylammonium hydroxide (TMA(OH)) aqueous solution, and is vigorously shaken. A resultant solution is centrifuged to separate an aqueous layer, and acetone is added. A resultant mixture is centrifuged at 8000 rpm to 12000 rpm for 5 minutes to 10 minutes, and a supernatant is removed to obtain a precipitate. 2 mL of 0.1% TMA(OH) solution is added and dispersed in the precipitate, acetone is added again in an amount of 10 mL, and a resultant mixture is left for precipitation. This operation can be repeated a plurality of times, and is repeated preferably 3 times to 4 times. A solution thus obtained is dispersed in 0.1% TMA(OH) solution and stored.

To 0.1% TMA(OH) solution thus prepared in accordance with the above procedure, a solution of the ligand compound, which solution is prepared with use of 0.1% to 2% TMA(OH) solution so as to achieve a pH of approximately 8 to 12, is added. A resultant solution is stirred at room temperature for 6 hours to 24 hours, and acetone is added. A resultant mixture is left for precipitation and is centrifuged at 8000 rpm to 12000 rpm for 3 minutes to 10 minutes, and a supernatant is removed. A precipitate thus obtained is dispersed in a phosphate buffer, and a resultant solution is centrifuged at 7000 rpm to 12000 rpm with use of a concentration column to reduce an amount of the solution. The phosphate buffer is added again, and a resultant mixture is centrifuged at 7000 rpm to 12000 rpm for 10 minutes to 20 minutes for concentration. This operation can be repeated a plurality of times, and is repeated preferably 3 times to 4 times, more preferably 5 times to 10 times. Thus obtained is a solution of an iron oxide particle coated with the ligand. The solution may be diluted with PBS and stored.

[3. Contrast Agent for Magnetic Resonance Imaging (Contrast Agent for MRI)]

The present invention also provides a contrast agent for magnetic resonance imaging which contrast agent includes the above-described nanoparticle.

The following description will discuss the contrast agent for MRI in detail.

(Various Components Contained in Contrast Agent for MRI)

=Nanoparticle=

In an embodiment of the present invention, the contrast agent for MRI of the present invention is characterized by containing at least one kind of the above-described nanoparticle. In another embodiment of the present invention, the contrast agent for MRI of the present invention may include a combination of two or more kinds of the above-described nanoparticle.

Further, the contrast agent for MRI may contain, if necessary, a solvent and a pharmacologically acceptable additive in addition to the nanoparticle. In an embodiment of the contrast agent for MRI of the present invention, the contrast agent may further contain a suitable solvent and/or at least one selected from additives such as a carrier, a vehicle, a complex and the like.

=Solvent=

Examples of the solvent contained in the contrast agent for MRI include water, a buffer solution, and the like. Further, examples of the buffer solution include physiological saline, phosphate buffer, tris buffer, boric acid buffer, Ringer's solution, and the like. In a case where a dosage form is an injection, examples of a preferable solvent include water, Ringer's solution, physiological saline, and the like.

That is, the contrast agent for MRI in accordance with the present invention may be a solution obtained by suspending the nanoparticle in accordance with the present invention in a solution having a desired composition. Specifically, the contrast agent may be in the form of a buffer solution such as phosphate buffer, tris buffer, or boric acid buffer in which the nanoparticle is suspended.

=Additive=

Examples of the additive such as a carrier, a complex, and a vehicle contained in the contrast agent for MRI include a carrier, a vehicle, and the like which are generally used in the fields of pharmaceuticals and biotechnology. Examples of the carrier include a polymer such as polyethylene glycol, a metal fine particle, and the like. Examples of the complex include diethylenetriaminepentaacetic acid (DTPA), 1,4,7,10-tetraazacyclododecane-1,4,7,10-tetraacetic acid (DOTA), and the like. Examples of the vehicle include lime, soda ash, sodium silicate, starch, glue, gelatin, tannin, quebracho, and the like.

Further, the contrast agent for MRI of the present invention may further contain an excipient, a lubricant, a wetting agent, an emulsifier, a suspension, a preservative, a pH adjusting agent, an osmotic pressure controlling agent, and the like.

(Dosage Form)

A dosage form of the contrast agent for MRI of the present invention is not particularly limited, and may be liquid, solid or semisolid, or semiliquid. These dosage forms can be produced easily in accordance with a method well known to a person skilled in the art. In a case where the dosage form is a liquid, the liquid may be one which is obtained by dispersing, suspending, or dissolving the nanoparticle in accordance with the present invention in, for example, an aqueous solvent so that the liquid contains the nanoparticle.

Further, the contrast agent may be in the form of a lyophilized agent, and be dispersed, suspended, or dissolved when used.

(Concentration of Nanoparticle)

A concentration of the nanoparticle in the contrast agent for MRI is determined as appropriate in accordance with a purpose, a tissue to be imaged, and the like. For example, a concentration is selected such that the selected concentration is in a range within which (i) an adequate contrast ability is exhibited and (ii) a degree of influence on a living organism is tolerable.

The nanoparticle of the present invention, even when contained at a high concentration, is less likely to be agglomerated and thus is capable of maintaining the stability. Accordingly, the nanoparticle of the present invention can maintain, stably and for a long period of time, a higher MRI contrast ability than a well-known nanoparticle.

For example, in a case where the contrast agent for MRI is a liquid that is an aqueous solution, examples of a concentration of the nanoparticle in the liquid when, for example, the liquid is used as a general injection include 0.1 mM Fe/mL to 1000 mM Fe/mL, preferably 1.0 mM Fe/mL to 500 mM Fe/mL, more preferably 5.0 mM Fe/mL to 100 mM Fe/mL, and, in an aspect, 10 mM Fe/mL to 500 mM Fe/mL, and, in another aspect, 5.0 mM Fe/mL to 50 mM Fe/mL.

(Administration Target)

An administration target to which the contrast agent in accordance with the present invention is administered can be, for example, a given organism that is not a human, or a human. Examples of the organism that is not a human include, but not limited to, mammals (e.g., rodents, mice, rats, rabbits, monkeys, dogs, cats, sheep, cows, primates, pigs, and the like), birds, reptiles, amphibians, fish, insects, and plants. In an aspect, the animal can be a transgenic animal, a genetically-engineered animal, or a clone animal. Further, the administration target can be one that is not a living organism, for example, a tissue sample or a biological material which includes a cell.

(Uses to which Contrast Agent for MRI is Applied)

As described above, there are two types of contrast agents for MRI, namely, a positive contrast agent and a negative contrast agent.

In an embodiment of the present invention, the contrast agent for MRI of the present invention is a positive contrast agent. In another embodiment, the contrast agent is a negative contrast agent.

The contrast agent for MRI of the present invention is used for, for example, diagnosis of a lesion and a tumor and the like using an MRI apparatus. For example, the contrast agent can be suitably used for examination of renal function, detection of liver tumors, hepatic angiography, and the like. Note that the MRI apparatus may be a given apparatus, and a well-known MRI apparatus can be used. A magnetic field to be applied may be, for example, 1 T, 1.5 T, 3 T, and 7 T. An example of a diagnosis method using the contrast agent of the present invention includes the steps of: administering a positive contrast agent to a living subject such as a human in vivo or in vitro; and subsequently forming an image of the subject with use of an MRI apparatus.

Among conventionally known contrast agents for MRI, a paramagnetic compound is used as a positive contrast agent, and a super paramagnetic nanoparticle is used as a negative contrast agent. The nanoparticle of the present invention is super paramagnetic, but can be used also as a positive contrast agent. Super paramagnetism is generated when a region containing a crystal having unpaired spins is large enough to be regarded as a single, thermodynamically independent domain particle called a "magnetic domain". The magnetic domain is a net magnetic dipole which is greater than a sum of individual unpaired electrons in the magnetic domain. While no magnetic field is applied, all magnetic domains are randomly oriented, and there is no net magnetization, accordingly. When an external magnetic field is applied, dipole moments in all magnetic domains are realigned. As a result, a net magnetic moment is generated. $T_1$, $T_2$, and $T_2^*$ relaxation processes are shortened by magnetic particles. In an embodiment of the present invention, the contrast agent in accordance with the present invention has a contrast ability represented by an $r_2$ relaxivity of 15 $mM^{-1}$ $s^{-11}$ to 19 $mM^{-1}$ $s^{-11}$ and an $r_1$ relaxivity of 9 $mM^{-1}$ $s^{-1}$ to 12 $mM^{-1}$ $s^{-1}$, at room temperature and with a magnetic field of 1 T. In another embodiment of the present invention, the contrast agent in accordance with the present invention has a contrast ability represented by an $r_2$ relaxivity of 5 $mM^{-1}$ $s^{-1}$ to 7 $mm^{-1}$ $s^{-1}$ and an $r_1$ relaxivity of 3 $mM^{-1}$ $s^{-1}$ to 5 $mM^{-1}$ $s^{-1}$, at room temperature and in a magnetic field of 1 T.

The relaxivity depends on various factors such as (i) a particle diameter of the metal particle in the nanoparticle of the contrast agent for MRI, (ii) a composition of the metal particle, (iii) a charge and properties of the surface of the particle, (iv) particle stability, and (v) agglomeration and connectivity to tissues in a living organism. A relaxivity ratio $r_1/r_2$ is generally used for quantification of a type of a contrast generated in MRI, and can serve as an index for performance of the contrast agent.

It is preferable that an $r_1/r_2$ value of the positive contrast agent for MRI of the present invention in a case where a magnetic field of 1 T is externally applied be as high as possible. For example, the $r_1/r_2$ value in a case where the magnetic field is 1 T is preferably 0.5 or more, more preferably 0.6 or more, and even more preferably 0.7 or more. In a case where the $r_1/r_2$ value is 0.5 or more, the positive contrast agent exhibits an excellent $T_1$ (positive) effect and, even in MRI measurement with a higher magnetic field, exhibits a high contrast effect with a high resolution. From the viewpoint of significantly increasing the contrast effect and reducing an amount of the positive contrast agent for MRI to be administered, the $r_1/r_2$ value is preferably 0.7 or more.

In the nanoparticle of the present invention, a molecular chain length of the ligand is shorter than that of a conventional ligand, and a ligand shell with which the core is coated is thinner. Thinness of the ligand shell reduces a distance between the metal particle serving as the core and a water molecule outside, and allows the relaxivity to be efficiently exhibited.

In the contrast agent for MRI of the present invention, the metal particle can have a particle diameter of 2 nm or less, or in an example, 1 nm or less. The contrast agent for MRI of the present invention can thus be utilized as a positive contrast agent with an MRI apparatus of 7 T or more. As an example, the contrast agent for MRI of the present invention encompasses a positive contrast agent for MRI to be used with an MRI apparatus of 7 T or less. As an example, the contrast agent for MRI of the present invention encompasses a positive contrast agent for MRI to be used with an MRI apparatus of 3 T or less.

(Toxicity and Stability)

The contrast agent for MRI of the present invention exhibits a high stability of the nanoparticle. As shown in Example 4 (described later), it has been confirmed that the contrast agent can be stored in a solution for a long period of time at room temperature or at 4° C. without undergoing agglomeration. Further, the contrast agent has a low toxicity to organisms. This allows for long-term and continuous application of the contrast agent to a living organism.

[4. Ligand Compound]

The present invention also relates to (3,4-dihydroxyphenyl) (dimethyl)(3-sulfonate propyl)ammonium represented by the above formula (2) and use of (3,4-dihydroxyphenyl) (dimethyl)(3-sulfonate propyl)ammonium for production of the nanoparticle.

The above compound can be used as a ligand for production of the nanoparticle of the present invention. Specifically, the compound is reacted with a metal particle coated with a hydrophilic ligand or the like to cause a ligand substitution reaction. This provides a nanoparticle in which the metal particle is coated with the ligand of the present invention which ligand has a structure represented by the following formula (1):

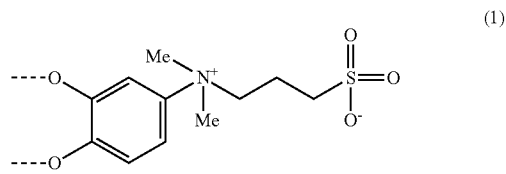

(1)

where a broken line represents a coordinate bond with a metal atom on the surface of the metal particle.

In an embodiment of the present invention, the compound in accordance with the present invention can be used as a ligand which is bound to a metal particle serving as a core in a nanoparticle made of (i) a metal selected from Fe, Gd, and Mn, (ii) a metal derivative thereof, and (iii) a combination of (i) and (ii). Examples of the metal derivative include an oxide, a nitride, a carbide, and a sulfide. For example, the metal particle and the compound are bound to each other by a coordinate bond between a metal atom on a surface of the metal particle and an oxygen atom.

In another aspect of the ligand compound in accordance with the present invention, the ligand compound is a compound represented by formula (4) below. In the above ligand substitution reaction, hydrogen ions are desorbed from two hydroxyl groups of the compound, and each remaining oxygen atom forms a coordinate bond with a metal atom on the surface of the metal particle. Thus produced is the nanoparticle of another aspect of the present invention.

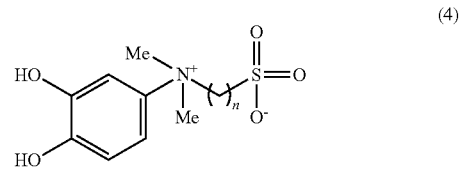

(4)

where n is an integer of 1 to 4.

A compound of another aspect of the present invention is a compound which is represented by the above formula (4) where n is 1, 2, or 4, preferably 2 or 4, and more preferably 4.

The compound represented by the above formula (4) is suitably used as a material for production of the nanoparticle of another aspect of the present invention which nanoparticle includes (i) a metal particle containing iron oxide and (ii) a ligand which is bound to a metal atom on a surface of the metal particle and is represented by the above formula (3).

[5. Examples of Specific Aspects in Accordance with the Present Invention]

In order to solve the above problem, the present invention includes in its scope any one aspect below.

<1> A nanoparticle including: a metal particle containing iron oxide; and a ligand which is bound to a metal atom on a surface of the metal particle and is represented by formula (3):

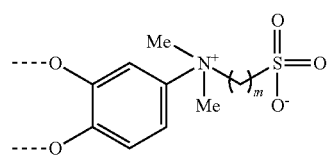

(3)

where m is an integer of 1 to 4, and a broken line represents a coordinate bond with a metal atom on the surface of the metal particle.

<2> The nanoparticle as set forth in <1> above, wherein the ligand bound to the metal atom on the surface of the metal particle is a ligand represented by the following formula (1):

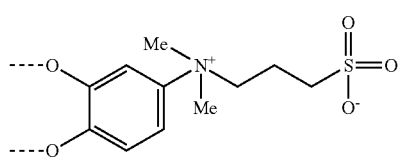

(1)

where a broken line represents a coordinate bond with the metal atom on the surface of the metal particle.

<3> The nanoparticle as set forth in <1> above, wherein m is 1, 2, or 4 in the above formula (3).

<4> The nanoparticle as set forth in any one of <1> through <3> above, wherein the metal particle containing the iron oxide is an iron oxide particle.

<5> The nanoparticle as set forth in any one of <1> through <4> above, wherein the metal particle has an average particle diameter of 5 nm or less.

<6> The nanoparticle as set forth in <5> above, wherein the metal particle has an average particle diameter of 4 nm or less.

<7> The nanoparticle as set forth in <5> above, wherein the metal particle has an average particle diameter of 3 nm or less.

<8> A contrast agent for magnetic resonance imaging, containing a nanoparticle recited in any one of <1> through <7> above.

<9> The contrast agent as set forth in <8> above, wherein the contrast agent is a positive contrast agent.

<10> Use of (3,4-dihydroxyphenyl)(dimethyl)(3-sulfonate propyl)ammonium for production of a nanoparticle recited in <2> above.

<11> (3,4-dihydroxyphenyl)(dimethyl)(3-sulfonate propyl)ammonium.

Further, the present invention includes in its scope the following aspects as other aspects of the present invention.

<12> A nanoparticle, including: a metal particle containing iron oxide; and a ligand which is bound to a metal atom on a surface of the metal particle and is represented by formula (1):

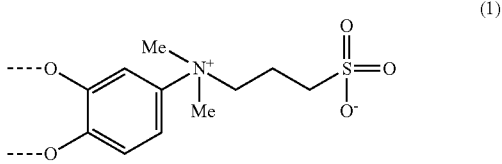

(1)

where a broken line represents a coordinate bond with the metal atom on the surface of the metal particle.

<13> The nanoparticle as set forth in <12> above, wherein the metal particle containing the iron oxide is an iron oxide particle.

<14> The nanoparticle as set forth in <12> or <13> above, wherein the metal particle has an average particle diameter of 5 nm or less.

<15> A contrast agent for magnetic resonance imaging, containing a nanoparticle recited in any one of <12> through <14> above.

<16> The contrast agent as set forth in <15> above, wherein the contrast agent is a positive contrast agent.

<17> Use of (3,4-dihydroxyphenyl) (dimethyl) (3-sulfonate propyl)ammonium for production of a nanoparticle recited in any one of <12> through <14> above.

<18> (3,4-dihydroxyphenyl) (dimethyl) (3-sulfonate propyl)ammonium.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

EXAMPLES

The following will provide Examples to describe the present invention in further detail.

Example 1. Synthesis 1 of Ligand Compound

According to the following Scheme 1, (3,4-dihydroxyphenyl) (dimethyl)(3-sulfonate propyl)ammonium (DDSA; Compound 3 of Scheme 1), which is a ligand compound of the present invention, was synthesized.

Scheme 1

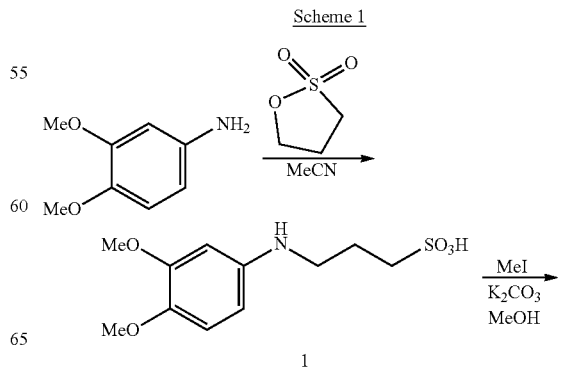

1

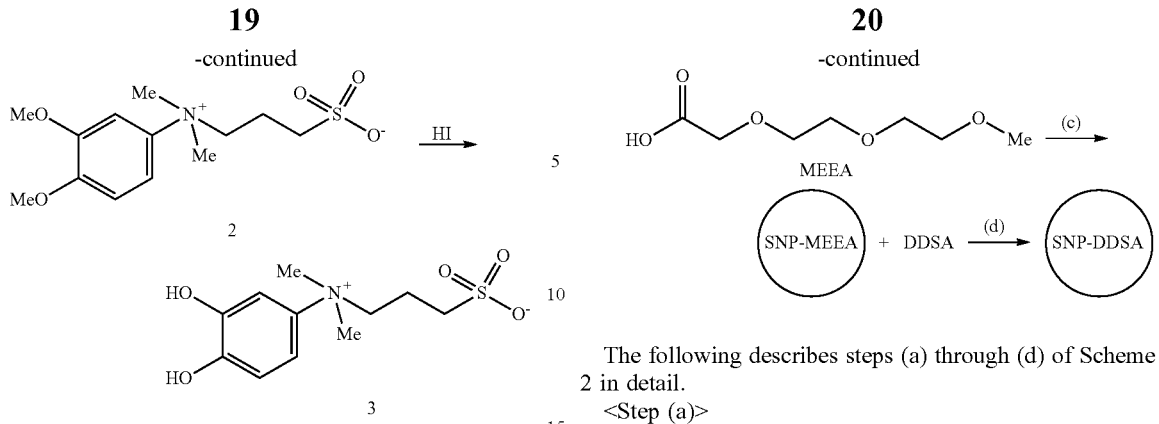

The following describes each step in detail.

1,3-propane sultone (5.98 g, 49.0 mmol) was added to acetonitrile (100 mL) solution of 3,4-dimethoxyaniline (5.00 g, 32.6 mmol), and a resultant mixture was stirred at room temperature in an argon atmosphere for 48 hours. A reaction mixture was filtered out, washed with acetonitrile, and then dried. Thus obtained was 3-(3,4-dimethoxyanilino)propane-1-sulfonic acid (Compound 1) in the form of grey powder (4.97 g, yield: 55%).

Compound 1 thus obtained (2.00 g, 7.26 mmol), potassium carbonate (2.01 g, 14.5 mmol), and iodomethane (8.25 g, 58.1 mmol) were dissolved in methanol (50 mL), and a resultant mixture was heated to reflux in an argon atmosphere for 12 hours. A reaction mixture was concentrated, and was purified by reversed phase column chromatography (water/acetonitrile). Thus obtained was (3,4-dimethoxyphenyl) (dimethyl) (3-sulfonate propyl)ammonium (Compound 2) (2.16 g, yield: 98%).

Compound 2 thus obtained (1.34 g, 4.42 mmol) was dissolved in hydriodic acid (10 mL), and a resultant mixture was heated to reflux in an argon atmosphere for 12 hours. A reaction mixture was heat-vacuum dried, and then water (10 mL) was added. Again, a solution thus obtained was heat-vacuum dried. Then again a resultant residue was dissolved in water (5 mL), and acetone (300 mL) was added. A resultant mixture was left for precipitation, and then a precipitate was filtered out. Thus obtained was (3,4-dihydroxyphenyl) (dimethyl)(3-sulfonate propyl)ammonium (DDSA, Compound 3) in the form of white powder (420 mg, yield: 35%).

Example 2. Production 1 of Nanoparticle

According to a procedure shown in Scheme 2, a nanoparticle (SNP-DDSA) which (i) included an iron oxide nanoparticle (SNP) having an average particle diameter of 1.8 nm and serving as a core particle and (ii) was coated with DDSA, was produced.

Scheme 2

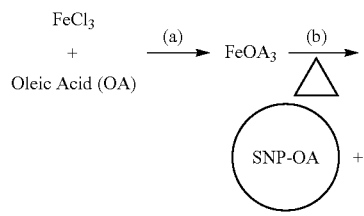

The following describes steps (a) through (d) of Scheme 2 in detail.

<Step (a)>

The step (a) is a step in which oleic acid (OA) is added to iron(III) chloride to produce a complex (FeOA$_3$) consisting of oleic acid and an iron ion.

Iron(III) chloride hexahydrate (2.16 g, 8 mmol), sodium oleate (7.3 g, 24 mmol), 16 mL of ethanol, 12 mL of water, and 28 mL of hexane were mixed in a 100-mL flask, and a resultant mixture was stirred at 70° C. for 4 hours. An organic layer was collected and transferred to a separatory funnel, 30 mL of water was added, the separatory funnel was vigorously shaken, and an organic layer was collected. This operation was repeated 3 times, and an organic layer obtained was dried. Thus obtained was a complex (FeOA$_3$) consisting of oleic acid and an iron ion.

<Step (b)>

The step (b) is a step in which FeOA$_3$ is reacted with oleyl alcohol to produce an iron oxide particle (SNP-OA) whose surface is coated with oleic acid.

To FeOA$_3$ (1.8 g, 2 mmol) obtained in the step (a), oleyl alcohol (3.22 g, 12 mmol) and 10 g of diphenyl ether were added in an Ar atmosphere. A resultant mixture was degassed at 90° C. while being stirred, and then was heated to 200° C. at a rate of 10° C./min. Stirring was continued at 200° C. for 30 minutes. Then, the mixture was cooled to room temperature, and 50 mL of acetone was added. A resultant mixture was centrifuged at 8000 rpm for 20 minutes, and a supernatant was removed. Until a precipitate obtained was completely dispersed, chloroform was added (approximately 0.5 mL). Further, 10 mL of acetone was added, then a resultant mixture was centrifuged at 8000 rpm for 20 minutes, and a supernatant was removed. This operation was repeated 3 times, and a supernatant obtained was dried.

<Step (c)>

The step (c) is a step in which oleyl acid, with which the surface of the SNP-OA obtained in the step (b) is coated, is substituted with 2-[2-(2-methoxyethoxy)ethoxy]acetic acid (MEEA) to produce a nanoparticle (SNP-MEEA) coated with a hydrophilic ligand.

In an Ar atmosphere, 10 mg of the SNP-OA was dispersed in 0.9 mL of methanol, and 0.1 mL of MEEA was added. A resultant mixture was stirred at 70° C. for 4 hours. A resultant solution was cooled to room temperature, and then 8 mL of acetone and 2 mL of hexane were added. A resultant mixture was centrifuged at 5800 rpm for 3 minutes, and a supernatant was removed. This operation was repeated 3 times, and a supernatant obtained was dried. Thus obtained was SNP-MEEA. Further, 300 μL of water and 600 μL of DMF were added to the SNP-MEEA. A resultant solution is hereinafter referred to as a "SNP-MEEA solution".

<Step (d)>

The step (d) is a step in which the SNP-MEEA obtained in the step (c) is reacted with (3,4-dihydroxyphenyl) (dimethyl)(3-sulfonate propyl)ammonium (DDSA) to produce a nanoparticle (SNP-DDSA) in which an iron oxide particle is coated with DDSA. Note that a DDSA ligand with which a surface of the iron oxide particle is coated in the nanoparticle (SNP-DDSA) has a structure represented by the following formula (1).

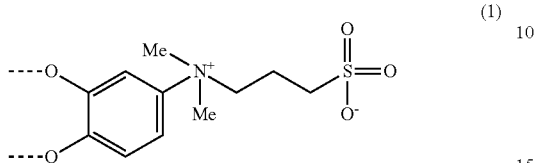

(1)

where a broken line represents a coordinate bond between an iron atom on the surface of the iron oxide particle and an oxygen atom.

85 mg of DDSA was added as a ligand compound to 1 mL of the SNP-MEEA solution in an Ar atmosphere, and a resultant mixture was stirred at 50° C. for 12 hours. Then, the mixture was cooled to room temperature, and 20 mL of acetone was added. A resultant mixture was centrifuged at 5800 rpm for 3 minutes, and a supernatant was removed. A precipitate obtained was dispersed in 2 mL of phosphate buffered saline (PBS). A solution obtained was centrifuged at 8000 rpm for approximately 30 minutes with use of Amicon Ultra centrifuge 3K filter (Merck Millipore, hereinafter abbreviated as "3K filter") to reduce a volume of the solution to approximately ⅕. PBS was added so that a total volume of a resultant solution was approximately 2 mL, and the solution was centrifuged. This operation was repeated approximately 5 times to 8 times until a solution dripping form the filter is completely colorless. A solution obtained was diluted with PBS so that a resultant solution had a volume of 1 mL to 1.5 mL. Thus obtained was an SNP-DDSA solution.

The SNP-DDSA solution obtained in the step (d) was stored at 4° C. Further, an iron concentration in the SNP-DDSA solution was determined by inductively coupled plasma-atomic emission spectroscopy (ICP-AES). FIG. 1 is an image of SNP-DDSA observed by a transmission electron microscope (TEM). From a result of observation with the TEM, it was estimated that, based on an average value of core diameters of 100 particles, the obtained SNP-DDSA had a diameter of an iron oxide particle, which serves as a core, of 1.8 nm on average.

Example 3. Evaluative Measurement of MR Relaxivity of Nanoparticle

The nanoparticle obtained in Example 2, SNP-DDSA, which included an iron oxide particle of 1.8 nm in diameter as a core, was used in an experiment below.

First, SNP-DDSA was diluted in PBS so as to change a concentration of SNP-DDSA in sequence. Solutions thus obtained were used as test samples. For each sample, a relaxivity was estimated by 1 T MRI.

First, $T_1$-weighted image was obtained in 1 T MRI. $T_1$ and $T_2$ measurement conditions are as follows.
<1 T MRI>
$T_1$-Weighted Image
Pulse Sequence: MSME, TR=400 msec, TE=10 msec, Slice Thickness=2 mm, Number of Slice=1, Matrix Size=256× 256, FOV=38.4×38.4 mm², scan time=1 min 42 sec.

$T_2$ Measurement (Multi Echo Spin Echo Technique)
Pulse Sequence: MSME, TR=15,000 msec, TE=20 msec (a cycle of TR and TE was repeated 256 times (using mao pulses)), Slice Thickness=2 mm, Number of Slice=1, FOV=38.4×38.4 mm², Matrix Size=64×64, Scan Time=16 min 00 sec.
$T_1$ Measurement (Inversion Recovery)
Pulse: SE-RARE, TR=20,000 sec, TE=17 msec, NEX=1, RARE Factor=4, Number of slice=1, slice thickness=2 mm, FOV=38.4×38.4 mm², Matrix Size=64×64. Scan Time per scan=21 min 20 sec, Inversion Time=45, 100, 200, 400, 800, 1600, 3200, 6400, 8000, 10000, 12000 (11 measurements)

Results are shown in FIG. 2. (a) of FIG. 2 illustrates a result of measurement of relaxation times in the PBS solutions of SNP-DDSA obtained by diluting SNP-DDSA in sequence. (b) of FIG. 2 is views each obtained by plotting a relaxation time with respect to an iron atom concentration in SNP-DDSA. It was confirmed from (b) of FIG. 2 that $T_1$ and $T_2$ were each in linear correlation with SNP concentration. (c) of FIG. 2 shows values of relaxivities $r_1$ and $r_2$ determined from an inclination of the plotted line in (b) of FIG. 2, and a $r_1/r_2$ value.

According to results of the above, the $r_1/r_2$ value at 1 T was 0.71. This value is the highest among $r_1/r_2$ values obtained with conventionally reported SNPs including an iron oxide particle as a core, after an influence of a magnetic field strength is corrected. This indicates that SNP-DDSA is promising to be applied to use as a positive contrast agent.

Example 4. Stability Evaluation Test

In order for a contrast agent containing a nanoparticle to exhibit an expected performance, it is necessary that the nanoparticle be stably dispersed in a solution. It is also desirable that dispersion of the nanoparticle is maintained for a long period of time even in a state where the nanoparticle is contained at a high concentration.

In general, a dispersion stability of a nanoparticle is evaluated by size exclusion chromatography (SEC) or dynamic light scattering (DLS).

SEC is an analysis technique in which (i) a sample is caused to run through a column filled with a carrier having pores and (ii) a size of the sample is estimated on the basis of a time it takes for the sample to be discharged from the column. Large aggregates do not enter the pores of the carrier, and therefore are quickly discharged from the column. Small nanoparticles pass through the pores of the carrier, and therefore are slowly discharged from the column due to following a longer route before being discharged from the column. It is thus possible to examine an agglomeration behavior on the basis of a change in time it takes for the sample to be discharged.

DLS is a method of estimating a hydrodynamic radius of an object in a solution on the basis of rates of temporal change in intensity and direction of light scattered by the object in the solution. It is possible to examine an agglomeration behavior on the basis of a distribution and an average value of the hydrodynamic radius obtained by this measurement.

In order to examine the stability of the nanoparticle, SNP-DDSA obtained in Example 2 above was freeze-dried and then was dispersed in PBS so as to achieve an Fe ion concentration of 100 mM. A solution thus obtained was used as a test sample.

The test sample was left to stand still at 4° C. and at room temperature (20° C.), respectively. 1 day, 7 days, and 28 days later, each test sample was subjected to SEC and DLS to check a degree of agglomeration. SEC measurement conditions and DLS measurement conditions were as follows.

<SEC Conditions>
Flow rate: 0.3 mL/min
Eluent: PBS
Column: Shodex KW403-4F
Detector: UV 280 nm, PDA 200 nm to 650 nm
<DLS Conditions>
Apparatus: Malvern Zetasizer nano
The solution was diluted so as to achieve an Fe ion concentration of approximately 1 mM, and was subjected to the measurement.

Observation of the subject by SEC and DLS for 28 days showed that, at both 4° C. and room temperature, (i) neither emergence of a new peak nor a shift of a peak occurred in the measurement by SEC and (ii) a distribution and an average value of the hydrodynamic radius hardly changed in the measurement by DLS. No agglomeration of SNP-DDSA was thus observed, and it was confirmed that the nanoparticle had an excellent stability.

Example 5. MRI Measurement Using Mouse

A contrast agent containing SNP-DDSA (a nanoparticle including an iron oxide particle of 1.8 nm in diameter as a core) produced in Example 2 was administered to a rat, and $T_1$-weighted images were obtained with use of an MRI device of 1 T. Measurement conditions were as follows.
Animal: C57BL/6j jms mouse, male, having a body weight of 27.8 g
Concentration of administered nanoparticle: 40 mM
Dosage: 200 µL
Magnetic field strength: 1 T
Imaging mode: $T_1$-weighted (FIGS. 3 through 5), MR angiography (FIG. 6)
Device used: 1 T MRI system (manufactured by Bruker Biospin, ICON, solenoid coil)
<1 T MRI>
$T_1$-Weighted Images
Pulse Sequence: MSME (Mulch Slice Mulch Echo), Slice Orient=Axial, TE/TR=10.464/400 msec, Field of view=40×40 mm², matrix size=256×256, Number of Slice=15, Slice thickness=1 mm, Slice Gap=2 mm, Number of averages=8, Scan Time=13 min 39 sec
<MR Angiography>
Pulse Sequence: FLASH (Fast Low Angle Shot), Slice Orient=Axial, TE/TR=5.954/15 msec, Field of view=28.8×28.8 mm², matrix size=192×192, Number of Slice=1, Slice thickness=1 mm, Number of averages=32, Scan Time=1 min 32 sec
Note that one slice of image was taken at 3 portions separately, since carrying out imaging at once would diminish signals from blood.

Imaging was carried out before the administration of the contrast agent, and then 200 µL of 40 mM SNP-DDSA solution was intravenously administered. Subsequently, imaging was carried out at different time points to conduct follow-up observation up to 3 hours after the administration. Results are shown in FIGS. 3 through 6.

(a) of FIG. 3 shows images of a bladder of the mouse to which the contrast agent containing SNP-DDSA of Example 2 was administered, which images were obtained as a result of MRI measurement carried out over time, respectively at the following timings: prior to the administration (pre), immediately after the administration (post), 30 minutes after the administration (30 min), and 3 hours after the administration (3 h). (b) of FIG. 3 shows images of the bladder of the mouse to which the contrast agent containing SNP-DDSA of Example 2 was administered, which images were obtained as a result of MRI measurement carried out over time, respectively at the following timings: prior to the administration (pre), immediately after the administration (post), 1 hour after the administration (1 h), and 2 hours after the administration (2 h). The fact that accumulation of urine was observed from immediately after the administration suggested that the contrast agent was excreted as urine from the kidney.

(a) of FIG. 4 shows images of a kidney of the mouse to which the contrast agent containing SNP-DDSA of Example 2 was administered, which images were obtained as a result of MRI measurement carried out over time, respectively at the following timings: prior to the administration (pre), immediately after the administration (post), 30 minutes after the administration (30 min), and 3 hours after the administration (3 h). (b) of FIG. 4 shows images of the kidney of the mouse to which the contrast agent containing SNP-DDSA of Example 2 was administered, which images were obtained as a result of MRI measurement carried out over time, respectively at the following timings: prior to the administration (pre), immediately after the administration (post), 1 hour after the administration (1 h), and 2 hours after the administration (2 h). The fact that both signals from the renal pelvis and signals from the renal cortex increased immediately after the administration suggested that the contrast agent was excreted as urine via the kidney. Further, observation of these changes in signals suggested that the contrast agent can be potentially used in a renal function test.

FIG. 5 shows images of a liver of the mouse to which the contrast agent containing SNP-DDSA of Example 2 was administered, which images were obtained as a result of MRI measurement carried out over time. Signals from the liver gradually decreased from immediately after the administration (in the images, portions that had originally looked whitish gradually darkened from immediately after the administration). This signal decrease is believed to have been caused by shortening of T2 relaxation time due to concentration and agglomeration of the contrast agent in a reticuloendothelial system of the liver. Since this phenomenon does not occur in the case of hepatoma, it was suggested that the contrast agent is useful for detecting a liver tumor.

Further, signals from many of the blood vessels of the liver increased. This suggested that the contrasting agent enables high-contrast imaging of blood vessels of the liver.

FIG. 6 shows images of blood vessels of the mouse to which the contrast agent containing SNP-DDSA of Example 2 was administered, which images were obtained as a result of MR angiography carried out over time.

In angiography, as indicated in the cross sections in FIG. 6, signals from veins increased immediately after the administration, and this state of signal increase continued for not less than 30 minutes.

Example 6. Synthesis 2 of Ligand Compound

According to the following Scheme 3, (3,4-dihydroxyphenyl) (dimethyl)(4-sulfonate butyl)ammonium (C4-DDSA; Compound 6), which is a ligand compound of another aspect of the present invention, in which aspect n=4 in the above formula (4), was synthesized.

Scheme 3

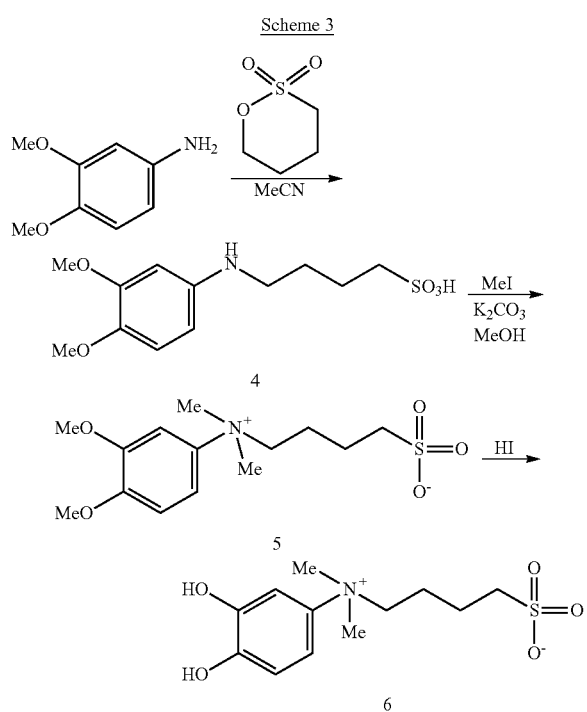

The following describes each step in detail.

1,4-butanesultone (1.60 mL) was added to a mixture of 3,4-dimethoxyaniline (2.00 g) and acetonitrile (50 mL), and a resultant mixture was stirred at 115° C. While stirring, 1,4-butanesultone (1.33 mL) was added twice. The stirring was performed for a total of 24 hours. After the mixture was cooled to room temperature, a solid was filtered out, was washed with acetonitrile, and then was dried at 50° C. under reduced pressure to obtain 4-(3,4-dimethoxyanilino)butane-1-sulfonic acid (2.97 g).

MASS (ESI+): 290

To a mixture of thus obtained Compound 4 (2.97 g), potassium carbonate (3.40 g), and methanol (45 mL), iodomethane (5.76 mL) was added. A resultant mixture was stirred at 50° C. for 3 days. The mixture was cooled to room temperature, and then was concentrated. An obtained residue was purified by reversed phase silica gel column chromatography (acetonitrile/water) to obtain (3,4-dimethoxyphenyl)(dimethyl)(4-sulfonate butyl)ammonium (3.12 g).

MASS (ESI+): 318

A mixture of thus obtained Compound 5 (3.12 g) and 57% hydriodic acid (13 mL) was stirred at 110° C. While stirring, 57% hydriodic acid (13 mL) was added. The stirring was performed for a total of 16 hours. After a resultant mixture was cooled to room temperature, water (20 mL) was added and a resultant mixture was concentrated. Water (20 mL) was added again, and a resultant mixture was concentrated. To an obtained residue, water (2 mL) and acetone (35 mL) were added. A resultant mixture was stirred for 30 minutes under ice-cooling, and a supernatant was discarded. Further, to an obtained residue, water (2 mL) and acetone (25 mL) were added, and a resultant mixture was stirred for 30 minutes under ice-cooling, and a supernatant was discarded. This operation was repeated one more time, and a resultant product was dried at 50° C. under reduced pressure to obtain (3,4-dihydroxyphenyl)(dimethyl)(4-sulfonate butyl)ammonium (C4-DDSA, Compound 6) (2.50 g).

MASS (ESI+): 290

1H NMR (DMSO-d6) δ ppm 1.36-1.57 (4H, m) 2.32-2.41 (2H, m) 3.41-3.48 (6H, m) 3.69-3.86 (2H, m) 6.86 (1H, d, J=8.8 Hz) 7.07 (1H, dd, J=8.8, 3.1 Hz) 7.23 (1H, d, J=3.1 Hz) 9.57 (1H, br s) 9.80 (1H, br s)

Example 7. Production 2 of Nanoparticle

According to the following Scheme 4, a nanoparticle (SNP-C4-DDSA) which included an iron oxide nanoparticle (SNP) serving as a core particle and was coated with C4-DDSA was produced.

Scheme 4

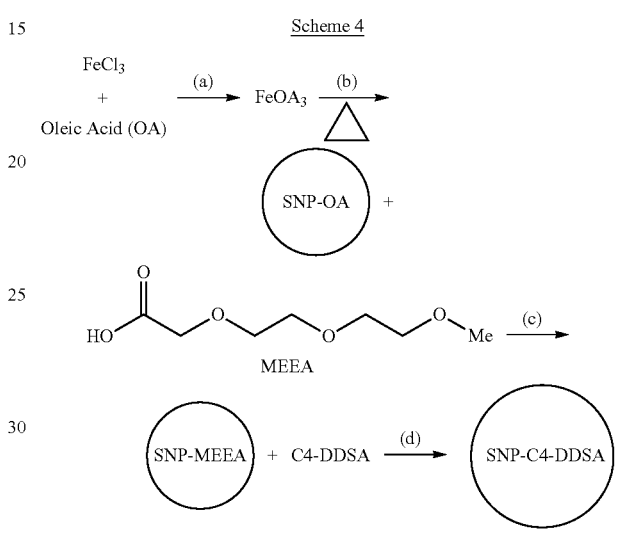

The following describes steps (a) through (d) of Scheme 4 above in detail.

<Step (a)>

The step (a) is a step in which oleic acid (OA) is added to iron(III) chloride to produce a complex (FeOA$_3$) consisting of oleic acid and an iron ion. The step (a) can be carried out in accordance with the step (a) in Scheme 2 described above.

<Step (b)>

The step (b) is a step in which FeOA$_3$ is reacted with oleyl alcohol to produce SNP-OA.

FeOA$_3$ (6.00 g), oleyl alcohol (10.7 g), and diphenyl ether (33.5 g) were added. A resultant mixture was degassed at 90° C. under reduced pressure for 2 hours while being stirred. Then, the pressure was changed to normal pressure with use of argon, and the mixture was heated to 230° C. over a period of 16 minutes and was stirred at 230° C. for 37 minutes (for 30 minutes after an internal temperature exceeded 220° C.). Then, the mixture was cooled to room temperature, and then hexane (5 mL) and acetone (150 mL) were added. A resultant mixture was centrifuged at 8000 rpm and 10° C. for 10 minutes, and a supernatant was removed. Hexane (24 mL) and acetone (150 mL) were added, a resultant mixture was centrifuged under the same conditions, and a supernatant was removed. This operation was repeated one more time to obtain SNP-OA (1.02 g).

<Step (c)>

The step (c) is a step in which oleyl acid, with which the surface of the SNP-OA obtained in the step (b) is coated, is substituted with MEEA to produce SNP-MEEA.

In an Ar atmosphere, a mixture of SNP-OA (20 mg), MEEA (500 uL), and methanol (1.5 mL) was stirred at 70° C. for 6 hours. After the mixture was cooled to room temperature, acetone (4 mL) and hexane (16 mL) were added, a resultant mixture was centrifuged at 7800 rpm and 10° C. for 10 minutes, and a supernatant was removed. This operation was repeated 3 times with use of acetone (1 mL) and hexane (4 mL) to obtain SNP-MEEA.

<Step (d)>

The step (d) is a step in which the SNP-MEEA obtained in the step (c) is reacted with C4-DDSA to produce a nanoparticle (SNP-C4-DDSA) in which an iron oxide particle is coated with C4-DDSA. Note that a DDSA ligand with which a surface of the iron oxide particle is coated in the nanoparticle (SNP-C4-DDSA) has a structure represented by the following formula (5).

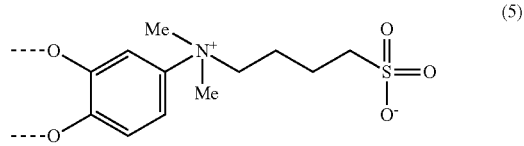

(5)

where a broken line represents a coordinate bond between an iron atom on the surface of the iron oxide particle and an oxygen atom.

C4-DDSA (250 mg) was dissolved in water (3.3 mL) while being heated, and sodium hydrogen carbonate (50 mg) was added. A resultant solution was added to the SNP-MEEA obtained in the step (c), and DMF (6.7 mL) was further added. A resultant mixture was stirred overnight at 50° C. The mixture was cooled to room temperature, and then water (1.5 mL) and acetone (60 mL) were added. A resultant mixture was divided into two portions, each of which was centrifuged at 7800 rpm and 10° C. for 10 minutes. A supernatant was removed. An obtained precipitate was dispersed in PBS, and a resultant solution was centrifuged at 5800 rpm and 10° C. for 30 minutes with use of Amicon Ultra centrifuge 100K filter (Merck Millipore). PBS was further added, and a resultant solution was centrifuged. This operation was repeated 3 more times. An obtained filtrate was centrifuged at 5800 rpm and 10° C. for 30 minutes with use of Amicon Ultra centrifuge 10K filter (Merck Millipore, hereinafter abbreviated as "10K filter"). Water was further added, and a resultant solution was centrifuged. This operation was repeated 3 more times. A resultant concentrated liquid was filtered through a YMC Duo-Filter (XQ DUO 15, pore size: 0.2 μm) and was freeze-dried to obtain SNP-C4-DDSA (10 K) (1.9 mg). A filtrate from the 10K filter was centrifuged at 5800 rpm and 10° C. for 1 hour with use of a 3K filter. Water was further added, and a resultant solution was centrifuged. This operation was repeated 8 more times. A resultant concentrated liquid was filtered through a YMC Duo-Filter and was freeze-dried to obtain SNP-C4-DDSA (3 K) (0.5 mg). Note that "(10K)" and "(3K)" following the term "SNP-C4-DDSA" each indicate a type of filter that was used last.

In a case where (3,4-dihydroxyphenyl)(dimethyl)(1-sulfonate methyl)ammonium (C1-DDSA), which is represented by the above formula (4) where n=1 or (3,4-dihydroxyphenyl) (dimethyl)(2-sulfonate methyl)ammonium (C2-DDSA), which is represented by the above formula (4) where n=2 are used as a ligand and combined with the steps of Scheme 2 or 4 above or with an equivalent or well-known technique, it is possible to produce (i) a nanoparticle (SNP-C1-DDSA) which includes an iron oxide nanoparticle (SNP) serving as a core particle and is coated with C1-DDSA or (ii) a nanoparticle (SNP-C2-DDSA) which includes an iron oxide nanoparticle (SNP) serving as a core particle and is coated with C2-DDSA, respectively.

INDUSTRIAL APPLICABILITY

A contrast agent for MRI of the present invention can be suitably used as a contrast agent for MRI in a medical field. A nanoparticle and a compound of the present invention are applicable to various pharmaceutical compositions and the like, including a contrast agent for MRI, and can be used widely in the fields of pharmaceuticals, biotechnology, and the like, including various diagnosis methods and examination reagents.

The invention claimed is:

1. A nanoparticle, comprising:
a metal particle containing iron oxide; and
a ligand which is bound to a metal atom on a surface of the metal particle and is represented by formula (3):

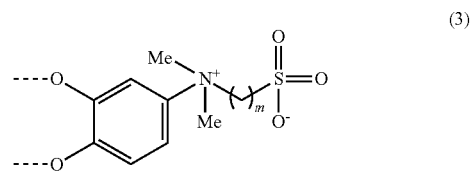

(3)

where m is an integer of 1 to 4, and a broken line represents a coordinate bond with a metal atom on the surface of the metal particle.

2. The nanoparticle as set forth in claim 1, wherein the ligand bound to the metal atom on the surface of the metal particle is a ligand represented by formula (1):

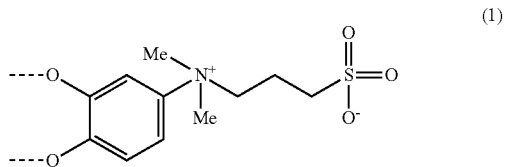

(1)

where a broken line represents a coordinate bond with the metal atom on the surface of the metal particle.

3. The nanoparticle as set forth in claim 1, wherein m is 1, 2, or 4 in the formula (3).

4. The nanoparticle as set forth in claim 1, wherein the metal particle containing the iron oxide is an iron oxide particle.

5. The nanoparticle as set forth in claim 1, wherein the metal particle has an average particle diameter of 5 nm or less.

6. The nanoparticle as set forth in claim 5, wherein the metal particle has an average particle diameter of 4 nm or less.

7. The nanoparticle as set forth in claim 5, wherein the metal particle has an average particle diameter of 3 nm or less.

8. A contrast agent for magnetic resonance imaging, comprising a nanoparticle recited in claim 1.

9. The contrast agent as set forth in claim 8, wherein the contrast agent is a positive contrast agent.

* * * * *